United States Patent
Kroll et al.

(10) Patent No.: US 7,684,870 B1
(45) Date of Patent: Mar. 23, 2010

(54) DIRECT CURRENT FIBRILLATOR

(75) Inventors: Mark W. Kroll, Orono, MN (US); J. Christopher Moulder, Encino, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 815 days.

(21) Appl. No.: 11/282,172

(22) Filed: Nov. 18, 2005

(51) Int. Cl.
*A61N 1/39* (2006.01)

(52) U.S. Cl. .............................. 607/72; 607/5

(58) Field of Classification Search ............... 607/4–8, 607/59, 72, 75, 76
See application file for complete search history.

(56) References Cited

U.S. PATENT DOCUMENTS

| | | | |
|---|---|---|---|
| 3,602,229 A * | 8/1971 | Jaros et al. ..................... 607/72 |
| 4,712,555 A | 12/1987 | Thornander et al. ... 128/419 PG |
| 4,788,980 A | 12/1988 | Mann et al. ........... 128/419 PG |
| 4,870,974 A * | 10/1989 | Wang ......................... 600/513 |
| 4,940,052 A | 7/1990 | Man et al. ............. 128/419 PG |
| 4,944,298 A | 7/1990 | Sholder ................ 128/419 PG |
| 5,117,834 A * | 6/1992 | Kroll et al. .................. 600/518 |
| 5,129,392 A * | 7/1992 | Bardy et al. .................... 607/2 |
| 5,215,083 A * | 6/1993 | Drane et al. .................... 607/4 |
| 5,222,501 A * | 6/1993 | Ideker et al. ................. 600/439 |
| 5,447,518 A * | 9/1995 | Pless ............................. 607/5 |
| 5,466,254 A | 11/1995 | Helland ...................... 607/123 |
| 5,476,483 A | 12/1995 | Bornzin et al. ................ 607/17 |
| 5,643,323 A | 7/1997 | Kroll et al. ..................... 607/2 |
| 5,649,971 A | 7/1997 | Fain et al. ..................... 607/72 |
| 5,653,740 A | 8/1997 | Degroot et al. ................ 607/72 |
| 5,824,018 A * | 10/1998 | Dreher et al. ................... 607/6 |
| 5,978,705 A * | 11/1999 | KenKnight et al. ............. 607/5 |
| 2004/0172068 A1* | 9/2004 | Sullivan et al. ................. 607/5 |
| 2004/0215248 A1* | 10/2004 | Hess ............................. 607/8 |

FOREIGN PATENT DOCUMENTS

WO    WO 97/26044    7/1997

\* cited by examiner

*Primary Examiner*—Carl H Layno
*Assistant Examiner*—Jessica Sarcione

(57) ABSTRACT

An implantable cardiac device to induce fibrillation in the heart of a patient to allow testing of the defibrillation capability of the device. The device induces fibrillation using a direct current across the heart. The shock to the heart may be applied in a method to minimize discomfort to the patient. The heart is monitored during application of the shock. The voltage of shock at the heart is gradually increased until fibrillation is induced. Once the fibrillation is detected the shock may be stopped. This results in a minimized voltage level and duration for the shock to the heart, thereby diminishing pain and discomfort to the patient.

19 Claims, 4 Drawing Sheets

DIRECT CURRENT FIBRILLATOR

TECHNICAL FIELD

The application relates generally to implantable cardiac stimulation devices, and more particularly relates to a device capable of inducing fibrillation in the heart of a patient to allow testing of the defibrillation capability of the device.

BACKGROUND

Implantable cardiac devices are well known in the art. They may take the form of implantable defibrillators or cardioverters, which treat accelerated rhythms of the heart such as fibrillation or implantable pacemakers, which maintain the heart rate within a prescribed limit, such as, for example, to treat a bradycardia. Implantable cardiac devices are also known which incorporate both a pacemaker and a defibrillator.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Implantable cardiac defibrillators (ICD's), encapsulated in a conductive housing or enclosure, are generally implanted in the left pectoral region of a patient and electrically connected to the heart with one or more electrode carrying leads. One lead includes at least one set of electrodes positioned in the right ventricle. An arrhythmia detector detects ventricular arrhythmias, such as ventricular fibrillation. When such an arrhythmia is detected, a pulse generator delivers a defibrillation output pulse from the defibrillation electrode in the right ventricle to the conductive housing to terminate the arrhythmia. Alternatively, such arrhythmia terminating systems may further include another defibrillation electrode arranged to be positioned in the right atrium and electrically connected to the right ventricular defibrillation electrode. In this arrangement, the defibrillation output pulse is delivered from the parallel connected right ventricular and right atrial electrodes to the conductive housing.

When ICDs are initially implanted their functionality is checked by inducing fibrillation in the heart of the patient and allowing the ICD to correct the condition. The process of inducing fibrillation applies a sudden direct current (DC) having a squared waveform and fixed duration to the heart. This sudden application of DC results in pain and discomfort for the patient, as the patient may be conscious although medicated. Inducement of fibrillation may also be used periodically after implant to recalibrate or check the function of the ICD. Fibrillation may be induced at the time that medication is changed to ensure that device is capable of defibrillating the heart when the patient is on the new medication.

SUMMARY

Embodiments include a method and apparatus for inducing fibrillation in a heart of a patient. A direct current shock may be applied to the heart of a patient to induce fibrillation. To alleviate pain caused by a sudden shock and the duration of the shock, the voltage applied to the heart is gradually ramped up or incremented until fibrillation is detected. At the time that fibrillation is detected, the shock to the heart is stopped to minimize the duration of the shock and therefore discomfort to the patient. Using the lowest voltage necessary also decreases pain and discomfort to the heart. After fibrillation is detected, the stimulation device is set to normal operation to treat the fibrillation and thereby confirm the operation of the stimulation device.

The stimulation device may include a fibrillation control unit to manage the application of the fibrillation inducing shock. The fibrillation control unit may manage the charging and shocking circuits of the stimulation device. The fibrillation control unit may be a subcomponent of a microcontroller in the stimulation device.

BRIEF DESCRIPTION OF THE DRAWINGS

Embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

Figure 1:
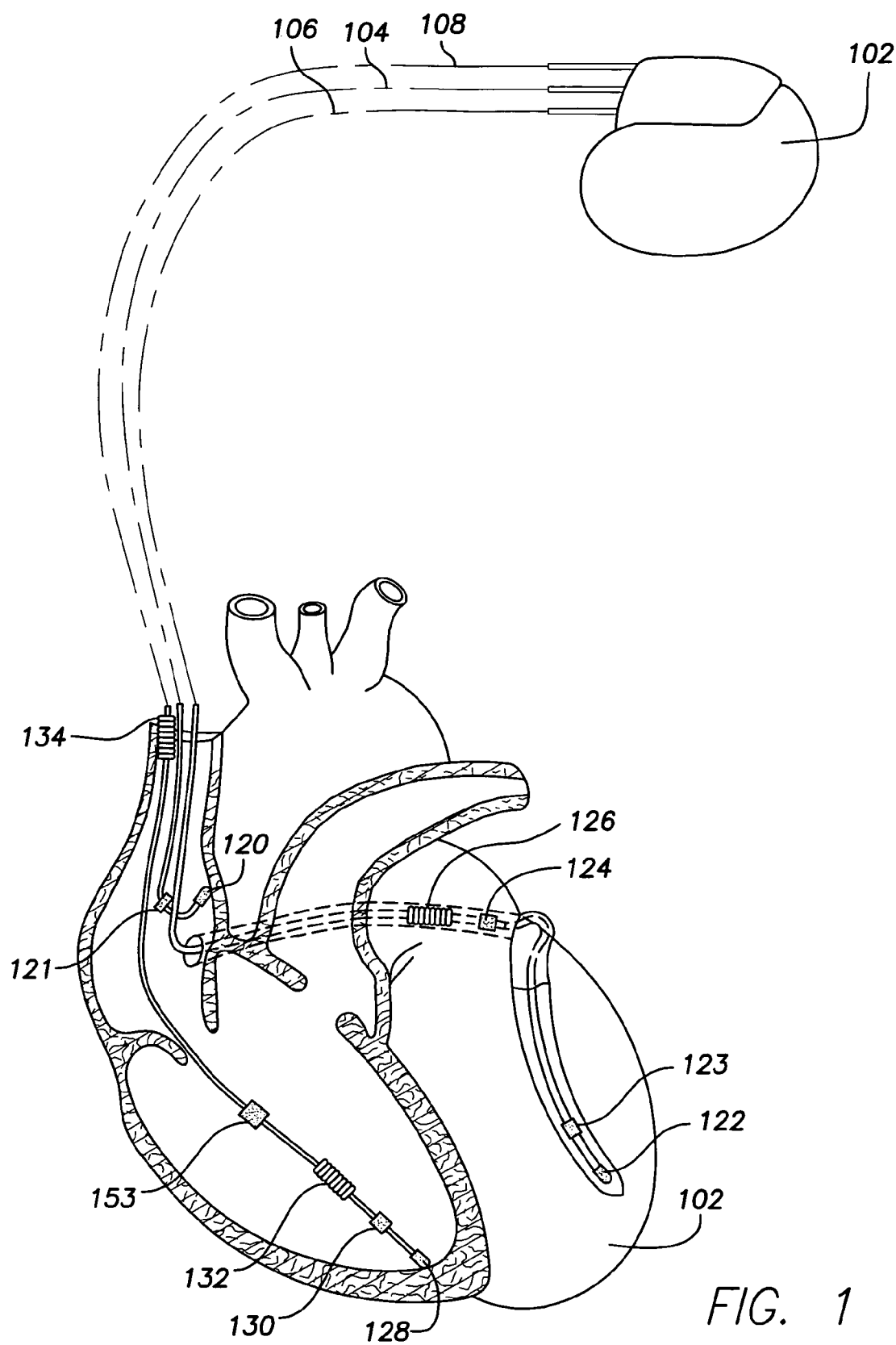
FIG. 1 is a simplified diagram illustrating an implantable stimulation device in electrical communication with leads implanted into a patient's heart for delivering multi-chamber stimulation and shock therapy.

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Also, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having, for example, an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy or fibrillation shocks using, for example, a left ventricular tip electrode 122, left ventricular ring electrode 123, left atrial pacing therapy using, for example, a left atrial ring electrode 124, and shocking therapy using, for example, a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy or fibrillating shocks to the right ventricle.

In one embodiment, other types of sensors may be attached to the leads to detect blood pressure, sense electrical signals or similar conditions in the heart. In one embodiment, a sensor 153 may be attached to a lead and be in electrical communication with the stimulation device 100. The sensor information may be used as input in determining pacing and detecting the condition of the heart and patient. The sensors may be pressure sensors, electrical sensors, hemodynamic sensors and similar sensors. Any number of sensors may be placed in any position throughout the heart and attached to any part of a lead including the body and tip of the lead.

Figure 2:
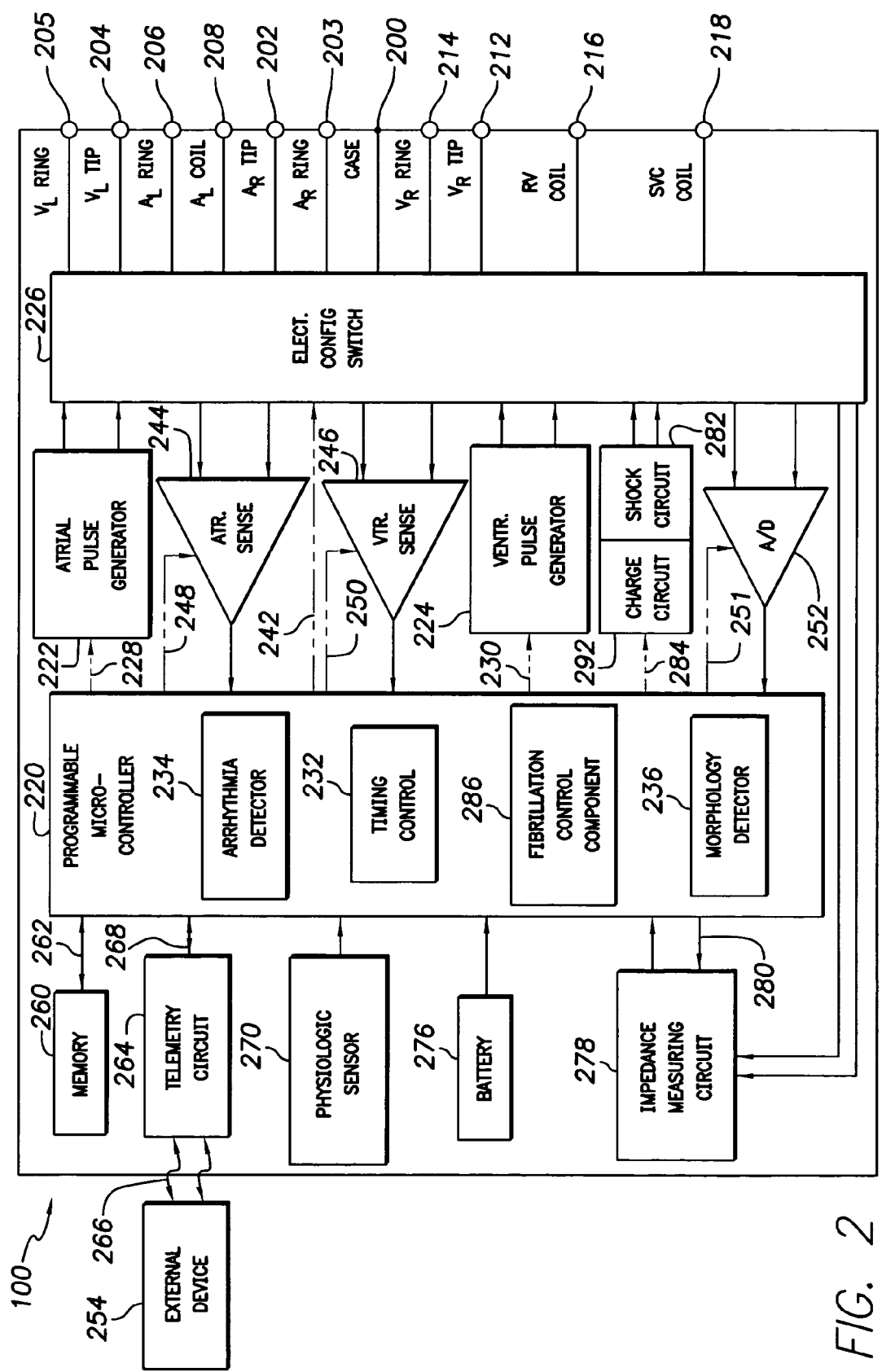
FIG. 2 is a functional block diagram of an implantable cardiac stimulation device embodying the present invention illustrating the basic elements thereof for providing fibrillation, cardioversion, defibrillation and pacing stimulation.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. In addition the stimulation device 100 may deliver a fibrillating shock to the heart to allow testing of the stimulation therapy capacity of the device. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes including applying fibrillating shocks. Housing 200 further includes a connector (not shown) having a plurality of terminals 202, 203, 204, 205, 206, 208, 212, 214, 216, and 218 (shown schematically and, for convenience, the names of the electrodes to which they are connected are shown next to the terminals).

To achieve right atrial sensing and pacing, the connector includes, for example, a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes, for example, a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" refers to receiving an electrical signal or obtaining data (information), and "detection" refers to the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are classified by the arrhythmia detector 234 of the microcontroller 220 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (ND) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiologic sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient.

Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiologic sensors 270 optionally include sensors to help detect movement and minute ventilation in the patient. The physiologic sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., for treatment, where the shock is in excess of 2 A, at voltages above 200 V, for periods of 10 seconds or more). The battery 276 also desirably has a predictable discharge characteristic so that elective replacement time can be detected. Accordingly, the device 100 preferably employs lithium or similar battery technology.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In one embodiment, the stimulation device 100 includes the capability of inducing fibrillation in a patient's heart to test the effectiveness and operation of the device for treating the condition. This feature may be utilized at the time of implant to test the stimulation device. To this end, the microcontroller 220 further includes a fibrillation control component 286 that controls a charging circuit 292 and shocking circuit 282 by way of a control signal 284. The charge circuit 282 accumulates and manages a set of charges in capacitors. Management of the charging circuit 292 may include initiating the charge of capacitors and setting the configuration of the capacitors (e.g., the capacitors may be used in isolation, in parallel or in series). The shocking circuit 282 applies shocking pulses using the stored energy of the capacitors, the shocking pulses may be of low (e.g., up to 0.5 J), moderate (e.g., 0.5 J to 10 J), or high energy (e.g., 11 J to 40 J), as set by the microcontroller 220, including the fibrillation control component 286. Such shocking pulses are applied to the patient's heart 102 through any combination of electrodes present electrically connected to the stimulation device. In one example, two shocking electrodes may be selected from the left atrial coil electrode 126, the RV coil electrode 132, and/or the SVC coil electrode 134. As noted above, the housing 200 may also act as an active electrode. For example, the housing 200 may be used in combination with the RV electrode 132, and/or as part of a split electrical vector using the SVC coil electrode 134 or the left atrial coil electrode 126 (e.g., using the RV electrode as a common electrode). Any combination of electrodes may be used to apply a shock. The combination of electrodes may be selected by the fibrillation control component 286 to effect a shock to induce fibrillation for testing purposes.

Fibrillation level shocks may be initiated at a low energy level and gradually increase in energy level. The escalation in energy level may be stopped and the shock ceases after fibrillation is induced or detected. Stopping the shock minimizes pain and discomfort for the patient. In one example, the shocks may be an application of direct current lasting two to five seconds, with a gradual increase of voltage from zero to nine volts at the heart or an increase of current in 0.1 to 0.5 increments at the shocking circuit. The duration of the shock and increase in voltage at the heart or increase in current in the shocking circuit is halted upon detection of fibrillation. In other embodiments, larger or smaller increments in adjusting the shocking circuit may be used or individually programmed for a patient. In another embodiment, the overall duration of the shock may be limited by a timer or similar mechanism.

Fibrillation level shocks may be applied to the heart along any vector. Any combination of electrodes may be used to apply the shock to the heart. The shock may also be applied along multiple vectors in succession. For example, the shock may be applied along a RV to case or SVC to case vector. As used herein, a shock may be a continuous application of voltage or current to the heart or may be a series of electrical pulses applied to the heart.

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In some embodiments device 100 also may include circuitry for processing signals from one or more pressure sensors. Depending upon the application, the pressure sensors may be implanted in the heart, in other locations in the patient such as the thoracic cavity, anywhere along a lead or within the housing 200.

Figure 3:
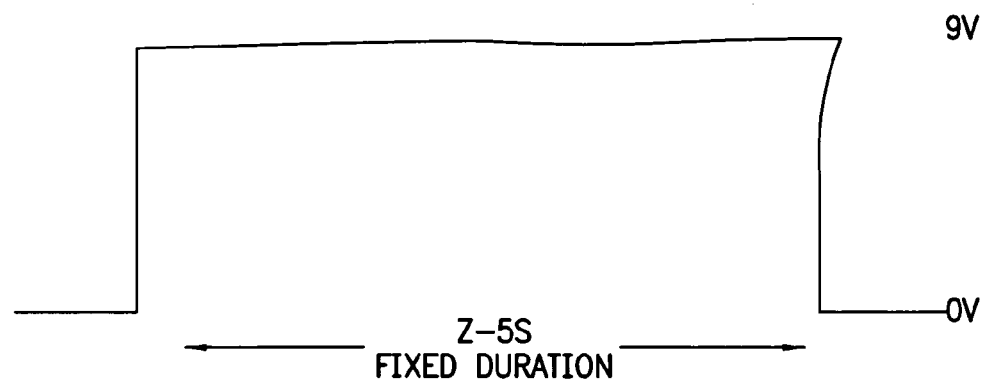
FIG. 3 is a diagram of a standard waveform generated by the stimulation device for inducing fibrillation.

FIG. 3 is a diagram of a standard waveform for applying direct current to a heart of patient to induce fibrillation. The standard waveform indicates that the shock to the patient's heart transitions directly from a level of zero volts to nine volts and remains at that voltage level for a predetermined amount of time. The predetermined amount of time may be from two to five seconds. The shock continues irrespective of fibrillation occurring in the heart. As a result, the patient experiences pain and discomfort from the sudden transition in voltage applied to the heart, from the high level of voltage applied and from the duration of the applied voltage.

Figure 4:
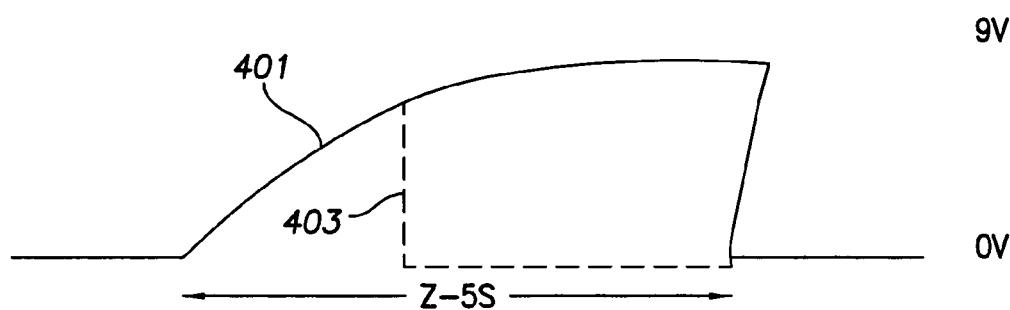
FIG. 4 is a diagram of one embodiment of a waveform generated by the stimulation device for inducing fibrillation.

FIG. 4 is a diagram of one embodiment of a gradually increasing waveform 401 used to induce fibrillation in the heart of a patient. In one embodiment, the voltage level of the shock applied to the heart may be gradually increased to induce fibrillation. The voltage may be increased from a starting point of zero volts up to nine volts. In one example embodiment, the voltage may be increased by increasing the current at the shocking circuit in 0.1 to 0.5 ampere increments or similar increments. The increase in current at the shocking circuit results in an increase in voltage at the heart of the patient. During the increase in voltage at the patient's heart, the microcontroller monitors the heart condition to detect fibrillation. For example, the standard arrhythmia detection component of the microcontroller or similar component may perform this function. At the time that fibrillation is detected, an indicator may be provided to the fibrillation control component to end the application of the shock to the patient. As a result the duration of the shock may be shortened causing the waveform to be altered into a shortened form 403. The gradual increase in voltage at the heart and halting of the shock when fibrillation is detected can diminish the duration of the shock and level of voltage applied during the shock. Shortening the shock and diminishing the voltage minimizes the level and duration of pain and discomfort experienced by the patient.

The waveform of the shock may be a gradual ramp, a gradual staircase, or similar waveform. The duration and voltage level of the waveform will differ from patient to patient depending on the unique characteristics of each patient. A short duration and low voltage may be sufficient to induce fibrillation in some patients while a higher voltage and longer duration may be necessary for others. In each case, a minimum voltage level and duration specific to the patient are applied.

Figure 5:
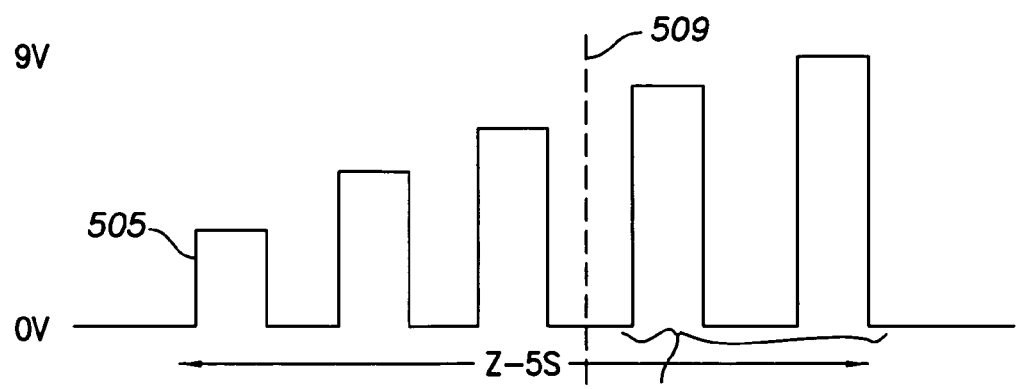
FIG. 5 is a diagram of one embodiment of a waveform generated by the stimulation device for inducing fibrillation.

FIG. 5 is a diagram of another embodiment of a waveform applied to induce fibrillation in the heart of a patient. In one embodiment, a gradual increase in voltage may be affected by short pulses of increasing voltage at the heart. In one example embodiment, each pulse 505 may have a duration of 100 to 300 milliseconds. Each gap between pulses may also have a duration of 100 to 300 milliseconds. For example, a signal with a fifty percent duty cycle may be applied, that is each pulse may be approximately 250 milliseconds and the gap between the pulses may be approximately 250 milliseconds. Each successive pulse may be increased by an increment in voltage starting at zero volts and progressing up to nine volts. The detection of fibrillation will cause the fibrillation control device to cease the generation of successive pulses. For example, if fibrillation is detected at a point in time 509 during the application of the fibrillation waveform, subsequent pulses 507 are not generated. There may be a lag between fibrillation and detection. In one embodiment, the total duration of the set of pulses may be between two and five seconds dependent on the detection of fibrillation in the heart of the patient.

Figure 6:
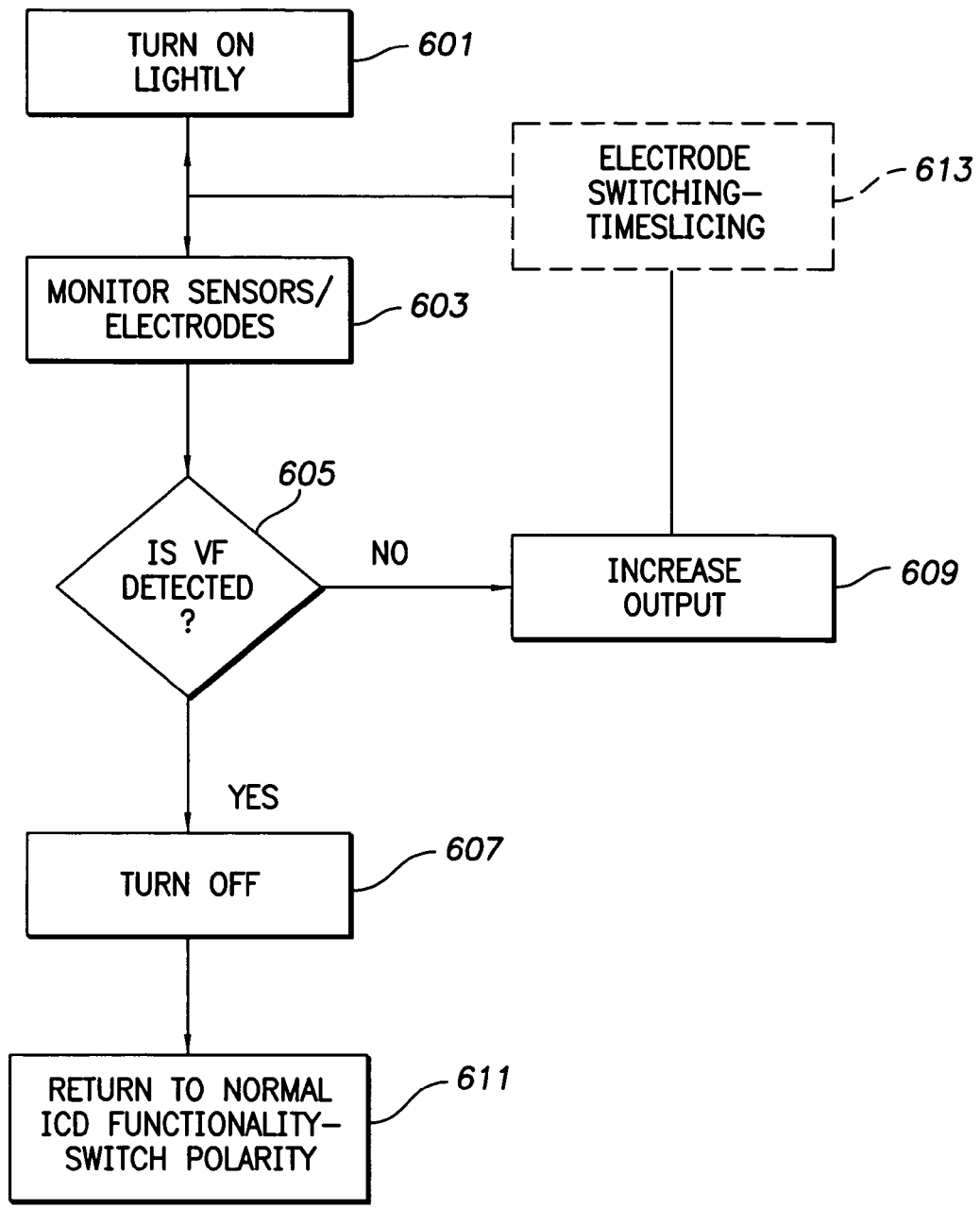
FIG. 6 is a flowchart of one embodiment of a process for inducing fibrillation in the heart of a patient.

FIG. 6 is a diagram of one embodiment of a process for managing the application of a shock to induce fibrillation in a heart of a patient. In one embodiment, the process may be initiated by a medical professional to test or calibrate the device (block 601). For example, the fibrillation inducing mode may be initiated at the time of implant to confirm the proper operation of the stimulation device. The fibrillation inducing mode may also be initiated periodically after implant to check the operational status, adjust the settings or calibrate the stimulation device.

The generation of a shock to the heart to induce fibrillation may be started by accumulating a charge in the capacitors of the stimulation device or checking to determine if a sufficient charge is available. Once a sufficient charge is available the shock may be applied to the heart by enabling the shocking circuit and selecting the desired set of electrodes to administer the shock to the heart. The first voltage level applied to the heart may be based on an initial increment of 0.1 to 0.5 amperes in the shocking circuit and applied to the electrodes.

In one embodiment, the multiple vectors may be utilized to induce fibrillation. Using multiple vectors increases the number of wavefronts that may be launched in a given period of time to improve the chances for inducing fibrillation. The multiple vectors may be implemented as a simultaneous mode and/or a time slice mode. For a simultaneous mode any combination of electrodes may be utilized. In one example a simultaneous mode may enable multiple sets of electrodes simultaneously. For example, an RV coil may be set as negative with respect to the case. At the same time, the left ventricular tip and ring may be paralleled to simulate a larger single electrode on the left side of the heart. In this example, the left ventricular pair is may function as a second cathode that launches additional wavefronts across the heart from the left side.

In another embodiment, the electrodes may be enabled in a time slice mode. Any combination of electrodes may be enabled during different time slices until ventricular fibrillation is detected. For example, an RV coil may be set to negative with respect to the case. At 100 ms intervals the left ventricular tip and ring may be enabled in parallel to simulate a larger single electrode on the left side of the heart. The left ventricular pair may become the cathode for a period of time, for example 5 ms. The RV coil may become the anode during this time slice to serve as a return path for the left ventricular pair electrical current.

The monitoring of sensor data in the heart may be initiated prior to the start of the shock, at the time the shock is started or thereafter. The sensors monitored to determine fibrillation may be far field sensors, electrodes implanted in the heart, hemodynamic sensors or similar sensors capable of detecting fibrillation in the heart during application of a fibrillation inducing shock (block 603). A hemodynamic sensor may detect changes or levels of blood flow or pressure.

Because the heart emits millivolt level signals, the sensors may have a −60 to −80 dB common mode rejection to enable detection of fibrillation during the application of the shock. The timing of the detection of fibrillation may not be tied directly to the application of the shock. The time required to detect fibrillation may vary dependent on the type of sensors utilized. For example, the use of far field sensing may require 0.5 seconds to detect fibrillation. Repeated or continuous detection may take place independent of the application of a fibrillating shock waveform or pulses, except that once fibrillation is detected an indicator may be provided to the fibrillation control component (block 605).

If fibrillation is not detected, then the output of the shocking circuit is increased (block 609). The increment of increase may be based on an increase of 0.1 to 0.5 amperes in the shocking circuit. If the voltage level at the heart reaches 9 volts, the current level and voltage may be held until fibrillation is induced. In one embodiment, increases in output voltages may be applied to all vectors in the multiple vector implementation and during all time slices. In another embodiment the voltages applied to different vectors or time slices may be varied. After and during the increase, monitoring of the sensors and detection of fibrillation may continue (blocks 603 and 605).

In an embodiment where time slicing is implemented, electrodes may be switched periodically (block 613). For example, electrodes may be switched at 100 ms intervals or may be switched intermittently from a standard setup to a secondary setup for 5 ms durations or similar timings and arrangements.

If fibrillation is detected, such as ventricular fibrillation (VT), then the shocking circuit and charging circuit may be disabled by the fibrillation control component (block 607). The stimulation device (e.g., an implanted cardiac device (ICD)) may return to normal function to treat the fibrillation and thereby confirm the operational status and settings of the stimulation device (block 611). In another embodiment, data related to the inducement of fibrillation may be stored or transmitted to an outside device. Stored or transmitted data may include vector, voltage, current and similar information related to the inducement of fibrillation. In one embodiment, when the device turns to normal operation the polarity of the device may be inverted. The switch of polarity may be set by the fibrillation control component or similar component of the microcontroller. A negative cathodal shock may be used to fibrillate the heart and an anodal shock may be used to defibrillate the heart. A cathodal shock from an electrode in direct contact with the heart tends to launch a large number of new wavefronts. This effect is proarrythmic. Therefore, anodal shocks are preferred for defibrillation to avoid this phenomenon. Conversely, this effect makes cathodal shocks well suited for inducing fibrillation.

In view of the above, it should be understood that a stimulation device may be constructed using various combinations and modifications of the structures, components and processes described herein. For example, the structure, components and processes described in a given drawing may be used in a fibrillation control component or process described in another drawing.

In addition, the structures described herein may be implemented in a variety of ways. For example, the fibrillation control component described herein may be software executed by the microcontroller, firmware or an application specific integrated circuit. Also, the combinations of some of the components which are described herein as being "attached," "connected" "including," "affixed," etc., may be implemented as one or more integral components.

It should be appreciated that the applications discussed herein regarding various embodiments may be applicable to other uses and contexts as well. For example, the treatment component and processes described above may be utilized in treating other heart conditions. Different embodiments of the external monitoring and control systems described above may include a variety of hardware and software processing components. In some embodiments of the invention, hardware components such as controllers, state machines and/or logic are used in a system constructed in accordance with the invention.

In some embodiments, code such as software or firmware executing on one or more processing devices may be used to implement one or more of the described operations. The signals between sensors and external devices may take several forms. For example, in some embodiments a signal may be an electrical signal transmitted over a wire while other signals may consist of wireless signals transmitted through space. In addition, a group of signals may be collectively referred to as a signal herein. The signals discussed above also may take the form of data. For example, in some embodiments an application program of an external device may send a signal to another application program. Such a signal may be stored in a data memory.

The invention described herein may be used as part of an improved implanted cardiac device capable of inducing fibrillation for testing and calibration purposes. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method comprising:
    constantly applying a current to a heart of a patient in accordance with a predetermined increasing waveform to induce fibrillation;
    monitoring the heart to detect fibrillation; and
    increasing the current applied to the heart of the patient in accordance with the predetermined increasing waveform until fibrillation has been detected;
    wherein the predetermined increasing waveform comprises a continuous, ramped and single pulse waveform.

2. The method of claim 1, further comprising:
    setting a cardiac device to a normal operating setting after fibrillation is detected.

3. The method of claim 2, further comprising:
    switching a polarity of the current after the cardiac device has returned to the normal operating setting.

4. The method of claim 1, further comprising;
turning a shocking circuit off after detecting fibrillation.

5. The method of claim 1, further comprising:
increasing an output of a shocking circuit by increments of 0.1 to 0.5 amperes in accordance with the predetermined increasing waveform.

6. The method of claim 1, wherein fibrillation is detected through classifying timing intervals between sensed events and comparing the timing intervals to a predefined rate zone limit and morphology characteristics.

7. The method of claim 1, wherein the current is applied as a cathodal shock to the heart.

8. The method of claim 1, wherein the current is applied to the heart through multiple vectors.

9. An apparatus comprising:
a set of electrodes configured for placement in electrical contact with a heart of a patient;
a sensor operative to detect a condition of the heart; and
a fibrillation control component operative to direct a generation of a shock for inducing fibrillation in the heart by constantly applying a current to the heart in accordance with a predetermined increasing waveform until fibrillation is detected;
wherein the predetermined increasing waveform comprises a continuous, ramped and single pulse waveform.

10. The apparatus of claim 9, further comprising:
a shocking circuit to generate the shock in accordance with the predetermined increasing waveform.

11. The apparatus of claim 10, wherein the fibrillation control component increments the shocking circuit in accordance with the predetermined increasing waveform by 0.1 to 0.5 amp steps until one of fibrillation is detected and 2 to 5 seconds elapses.

12. The apparatus of claim 9, wherein the sensor is a hemodynamic sensor.

13. The apparatus of claim 9, wherein the set of electrodes includes a ventricular ring electrode and ventricular tip electrode.

14. The apparatus of claim 9, further comprising:
a monitoring circuit to detect fibrillation in the heart and signal the fibrillation control component.

15. The apparatus of claim 14, wherein the fibrillation control component receives the signal from the monitoring circuit and directs a cessation of the generation of the shock in accordance with the predetermined increasing waveform.

16. The apparatus of claim 9, wherein the fibrillation control component sets an implanted cardiac device to normal operation on detection of fibrillation.

17. The apparatus of claim 9, wherein the fibrillation control component enables the shock to be applied along multiple vectors in accordance with the predetermined increasing waveform.

18. The apparatus of claim 9, wherein the shock generated by the fibrillation control component is cathodal.

19. The apparatus of claim 9, wherein the fibrillation control component is further operative to direct a generation of a shock for providing defibrillation to treat the induced fibrillation, and wherein the shock generated for providing defibrillation is anodal.

* * * * *